(12) United States Patent
Czer

(10) Patent No.: US 8,523,780 B2
(45) Date of Patent: Sep. 3, 2013

(54) ELECTRONIC DEVICE AND SYSTEM FOR DETECTING REJECTION IN TRANSPLANT RECIPIENTS

(75) Inventor: Lawrence S. C. Czer, Santa Monica, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 496 days.

(21) Appl. No.: 12/523,599

(22) PCT Filed: Jan. 17, 2008

(86) PCT No.: PCT/US2008/051301
§ 371 (c)(1),
(2), (4) Date: Jul. 17, 2009

(87) PCT Pub. No.: WO2008/089323
PCT Pub. Date: Jul. 24, 2008

(65) Prior Publication Data
US 2010/0016684 A1      Jan. 21, 2010

Related U.S. Application Data

(60) Provisional application No. 60/885,510, filed on Jan. 18, 2007.

(51) Int. Cl.
*A61B 5/0402*           (2006.01)

(52) U.S. Cl.
USPC .......................................................... 600/508

(58) Field of Classification Search
None
See application file for complete search history.

(56) References Cited

U.S. PATENT DOCUMENTS

| | | | |
|---|---|---|---|
| 7,826,895 B2 * | 11/2010 | Parsonnet et al. | 600/547 |
| 2005/0113705 A1 * | 5/2005 | Fischell et al. | 600/515 |
| 2006/0036286 A1 * | 2/2006 | Whitehurst et al. | 607/3 |
| 2007/0016089 A1 * | 1/2007 | Fischell et al. | 600/509 |
| 2009/0210020 A1 * | 8/2009 | Feldman et al. | 607/4 |

* cited by examiner

*Primary Examiner* — Carl H Layno
*Assistant Examiner* — Paula J Stice
(74) *Attorney, Agent, or Firm* — Linda B. Huber; Nixon Peabody LLP

(57) ABSTRACT

The current invention relates to an implantable device, system, method, and computer readable medium comprising computer executable components for detection of rejection of a cardiac allograft. Acute rejection and chronic rejection are the leading cause of death in heart transplant recipients post transplant. The current invention seeks to address this problem by providing methods, devices, systems and computer readable media comprising computer executable components to monitor the efficacy of immunosuppressant therapy and evaluate the degree of rejection in a cardiac allograft. To provide this functionality, an implantable device comprises sensors which measure physiologic parameters at specified intervals after the transplant procedure. These measured parameters are subsequently compared with baseline parameter data to detect rejection of the cardiac allograft.

39 Claims, 4 Drawing Sheets

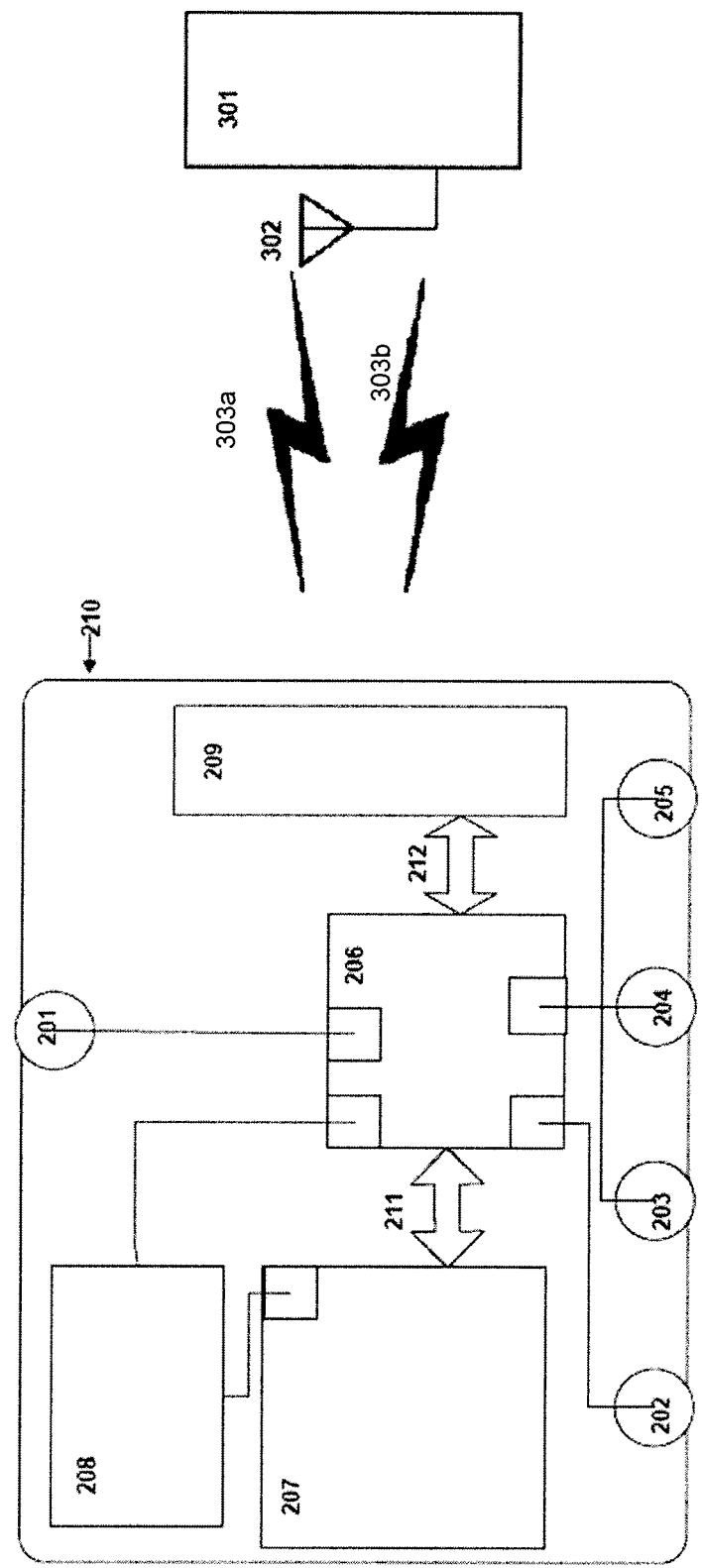

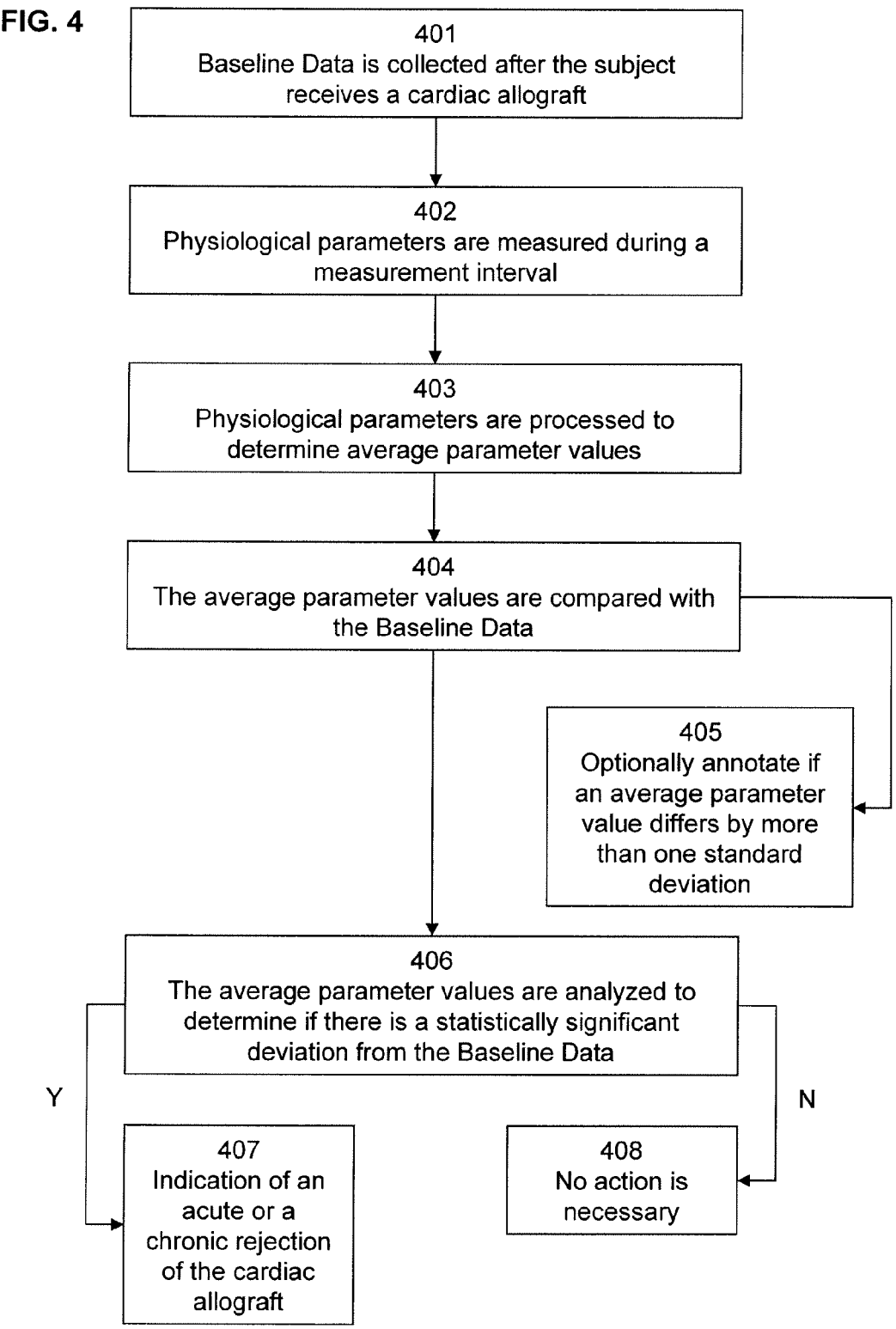

ELECTRONIC DEVICE AND SYSTEM FOR DETECTING REJECTION IN TRANSPLANT RECIPIENTS

This application is the National Phase of International Application PCT/US08/51301, filed Jan. 17, 2008, which designated the U.S. and that international Application was published under PCT Article 21(2) in English. This application also includes a claim of priority under 35 U.S.C. §119(e) to U.S. provisional patent application No. 60/885,510, filed Jan. 18, 2007.

FIELD OF INVENTION

This invention relates to the detection of cardiac allograft rejection.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

When a patient is at end stage heart failure or suffers from severe coronary artery disease, the patient faces limited treatment options. The most effective treatment for these patients is heart transplantation, where the patient's diseased heart is replaced with a healthy heart from a deceased donor. The short term survival rate for patients receiving a heart transplant is high, approaching 85% of patients one year after transplantation. Despite improvements prolonging the short term survival of heart transplant recipients, the long term graft survival rate remains poor, dropping to under 50% after 10 years.

The leading cause of death after heart transplantation is allograft rejection, either chronic or acute, where the recipient's immune system attacks the transplanted organ. To combat allograft rejection, recipients of a heart transplant must take a regimen of immunosuppressant drugs for the remainder of their life. However, immunosuppressant drugs are not without their side effects. In addition to preventing allograft rejection, the administration of immunosuppressant drugs also weakens a transplant recipient's immune system. As a result, the transplant recipient has an inhibited ability to ward off common colds, infections and other illness. To mitigate the effects of immunosuppressant therapy, the dosage the transplant recipient receives is limited as much as possible. The balance between limiting the dosage of the immunosuppressant regimen and combating transplant rejection is maintained by constant monitoring of the transplant recipient to guide immunosuppressant therapy.

Currently, the standard method for monitoring rejection of a cardiac allograft is through endomyocardial biopsy. These biopsies are typically performed once a week initially, and slowly taper over time to a frequency of once every three to six months. During an endomyocardial biopsy, the patient is administered a local anesthetic, and a special type of catheter called a biotome is inserted into a vein in the patient's neck or groin. The biotome is guided into the right side of the patient's heart, where it takes approximately four tissue samples from one to four millimeters in size from the right ventricular septum. These tissue samples are analyzed under a microscope to determine the degree of rejection in the allograft, which is indicated by the infiltration of mononuclear cells in the allograft tissue, and the extent of interstitial fibrosis and myocyte degeneration.

Despite its widespread use, endomyocardial biopsy has several serious limitations. Namely, the procedure can only detect cardiac allograft rejection after cellular infiltration and/or significant graft damage have occurred. In addition, the procedure is expensive, costing approximately $1200 to $4000 per procedure, as well as invasive and uncomfortable for patients. Furthermore, such tests cannot be conducted remotely as they require office or hospital visits. Consequently, there exists a need in the art for alternative methods for detection of cardiac allograft rejection.

SUMMARY OF THE INVENTION

The following embodiments and aspects thereof are described and illustrated in conjunction with compositions and methods which are meant to be exemplary and illustrative, not limiting in scope.

The present invention describes a method for detecting cardiac allograft rejection in a subject that has received a cardiac allograft, comprising: determining baseline data regarding the subject and the cardiac allograft; measuring at least one parameter of the cardiac allograft during a measurement interval; determining at least one average parameter value for the at least one parameter during the measurement interval; and comparing the at least one average parameter value with the baseline data to detect the presence of a cardiac allograft rejection, wherein the at least one parameter may be selected from the group consisting of electrical activity generated by the cardiac allograft, at least one voltage generated by the cardiac allograft, rate of change of the at least one voltage generated by the cardiac allograft, impedance within the chest, body temperature and combinations thereof. In an embodiment wherein the at least one parameter is impedance within the chest, the impedance is used to calculate cardiac output, lung water content or both.

In a further embodiment, the method may comprise providing an implantable device for detecting rejection of the cardiac allograft in the subject, comprising: a plurality of sensors to measure the at least one parameter; a processor in electronic communication with the plurality of sensors, the processor configured to receive at least one measured parameter; a memory component to store the baseline data, data corresponding to the at least one measured parameter and/or data corresponding to the at least one average parameter value; and a power supply component to provide electricity to components of the implantable device.

In one embodiment, the method may further comprise determining a presence of a statistically significant deviation from the baseline data, whereby the presence of the statistically significant deviation is indicative of an acute or a chronic rejection episode. In another embodiment, the method may further comprise annotating the at least one average parameter value if the at least one parameter value differs by more than one standard deviation from the baseline data. Alternatively, at least one average parameter value may be annotated if the at least one parameter value differs by more than two standard deviations from the baseline data.

In a further embodiment, collecting the data used to determine the baseline data begins about five days after a cardiac allograft transplant procedure.

In another embodiment, determining the baseline data may comprise collecting data for about thirty minutes a day for a period of about one week and determining the average values of the data. In various embodiments, the measurement interval may be selected from the group consisting of about 50, 100, 200, 300, 400, 500, and 1000 contraction cycles of the cardiac allograft. In a particular embodiment, the measurement interval is about one hundred contraction cycles of the cardiac allograft. In other embodiments, the measurement interval may be selected from the group consisting of about 0.5, 1, 2, 3, 4, 5, 10, 15, 20, 30, 45, and 60 minutes.

The present invention also describes an implantable device for detecting cardiac allograft rejection in a subject that has received a cardiac allograft, comprising: a plurality of sensors to measure at least one parameter; a processor in electronic communication with the plurality of sensors, the processor configured to receive at least one measured parameter; a memory component to store baseline data, data corresponding to the at least one measured parameter and/or data corresponding to at least one average parameter value; a power supply component to provide electricity to components of the implantable device; and a housing to encapsulate components of the implantable device, wherein the at least one parameter may be selected from the group consisting of electrical activity generated by the cardiac allograft, at least one voltage generated by the cardiac allograft, rate of change of the at least one voltage generated by the cardiac allograft, impedance within the chest, body temperature and combinations thereof. In embodiments wherein the body temperature is measured, the at least one sensor may be selected from the group consisting of a thermocouple, a thermistor, a resistance thermometer and combinations thereof.

In one embodiment, the implantable device may further comprise a transmitting component to transmit the data corresponding to the at least one measured parameter to an external device.

In another embodiment, the processor may be further configured to determine the at least one average parameter value for the at least one parameter during a measurement interval. In various embodiments, the measurement interval may be selected from the group consisting of about 50, 100, 200, 300, 400, 500, and 1000 contraction cycles of the cardiac allograft. In a particular embodiment, the measurement interval may be about one hundred contraction cycles of the cardiac allograft. In other embodiments, the measurement interval may be selected from the group consisting of about 0.5, 1, 2, 3, 4, 5, 10, 15, 20, 30, 45, and 60 minutes.

The present invention additionally describes an external device adapted to communicate with an implantable device for detecting cardiac allograft rejection, the implantable device comprising: a plurality of sensors to measure at least one parameter; a processor in electronic communication with the plurality of sensors, the processor configured to receive at least one measured parameter; and a memory component to store baseline data, data corresponding to the at least one measured parameter and/or data corresponding to at least one average parameter value, wherein the at least one parameter may be selected from the group consisting of electrical activity generated by the cardiac allograft, at least one voltage generated by the cardiac allograft, rate of change of the at least one voltage generated by the cardiac allograft, impedance within the chest, body temperature and combinations thereof.

In one embodiment, the external device is further adapted to receive and analyze the at least one average parameter value to determine a presence of a statistically significant deviation from baseline data, whereby the presence of the statistically significant deviation is indicative of an acute or chronic rejection episode. In another embodiment, the external device is further adapted to receive information regarding the presence of a statistically significant deviation from the baseline data that is indicative of an acute or chronic rejection episode. In another embodiment, the external device is further adapted to provide an alert regarding the rejection of the cardiac allograft.

The present invention further describes a system for detecting cardiac allograft rejection in a subject that received a cardiac allograft, comprising: an implantable device for detecting cardiac allograft rejection as described herein and an external device adapted to communicate with the implantable device as described herein.

The present invention further describes a computer readable medium to detect cardiac allograft rejection in a subject that has received a cardiac allograft, comprising computer executable components for: determining baseline data regarding the subject and the cardiac allograft; measuring at least one parameter of the cardiac allograft during a measurement interval; determining at least one average parameter value for the at least one parameter during the measurement interval; and comparing the at least one average parameter value with the baseline data to detect the presence of a cardiac allograft rejection, wherein the at least one parameter may be selected from the group consisting of electrical activity generated by the cardiac allograft, at least one voltage generated by the cardiac allograft, rate of change of the at least one voltage generated by the cardiac allograft, impedance within the chest, body temperature and combinations thereof. In various embodiments, the measurement interval may be selected from the group consisting of about 50, 100, 200, 300, 400, 500, and 1000 contraction cycles of the cardiac allograft. In one particular embodiment, the measurement interval may be about one hundred contraction cycles of the cardiac allograft. In other embodiments, the measurement interval may be selected from the group consisting of about 0.5, 1, 2, 3, 4, 5, 10, 15, 20, 30, 45, and 60 minutes.

In one embodiment, the computer readable medium may further comprise a computer executable component for determining a presence of a statistically significant deviation from the baseline data, whereby the presence of the statistically significant deviation is indicative of an acute or a chronic rejection episode. In another embodiment, the computer readable medium may further comprise a computer executable component for annotating the at least one average parameter value if the at least one parameter value differs by more than one standard deviation from the baseline data. In another embodiment, the computer readable medium may further comprise a computer executable component for annotating the at least one average parameter value if the at least one parameter value differs by more than two standard deviations from the baseline data. In a further embodiment, the computer readable medium may comprise a computer executable component for calculating cardiac output, lung water content or both.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are considered illustrative rather than restrictive.

FIG. 3 depicts a system for detecting cardiac allograft rejection in accordance with an embodiment of the present invention.

FIG. 4 depicts a flow chart representative of a method for detecting cardiac allograft rejection in accordance with an embodiment of the present invention.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Baseline data" as used herein refers to average physiological parameters regarding a subject and a cardiac allograft after a transplant procedure to which subsequent measured parameters are compared to detect cardiac allograft rejection.

"Measurement interval" as used herein refers to a period during which physiological parameters regarding a subject and the cardiac allograft are collected. Examples of measurement intervals include but are not limited to a set number of contraction cycles of the heart (e.g., 50, 100, 200, 300, 400, 500, or 1000 contraction cycles and a set period of time (e.g., 30 seconds, 1, 2, 3, 4, 5, 10, 15, 20, 30, 45, or 60 minutes).

"Electrical activity" as used herein regarding a heart or a cardiac allograft refers to voltages generated by the cardiac allograft and the various waves and vectors of depolarization and repolarization.

The current invention relates to methods, devices, systems and computer readable media having computer executable components to detect rejection of a cardiac allograft. Acute rejection and chronic rejection are the leading cause of death in heart transplant recipients post transplant. The current invention seeks to address this problem by providing methods, devices, systems and computer readable media having computer executable components to monitor the efficacy of immunosuppressant therapy and evaluate the degree of rejection of a cardiac allograft. To provide this functionality, an implantable device comprises sensors which measure physiological parameters, such as core body temperature, cardiac output, and electrical activity (e.g., voltages) generated by the cardiac allograft, at specified intervals after the transplant procedure. These measured parameters are subsequently compared with baseline data to detect rejection of the cardiac allograft.

Figure 1:
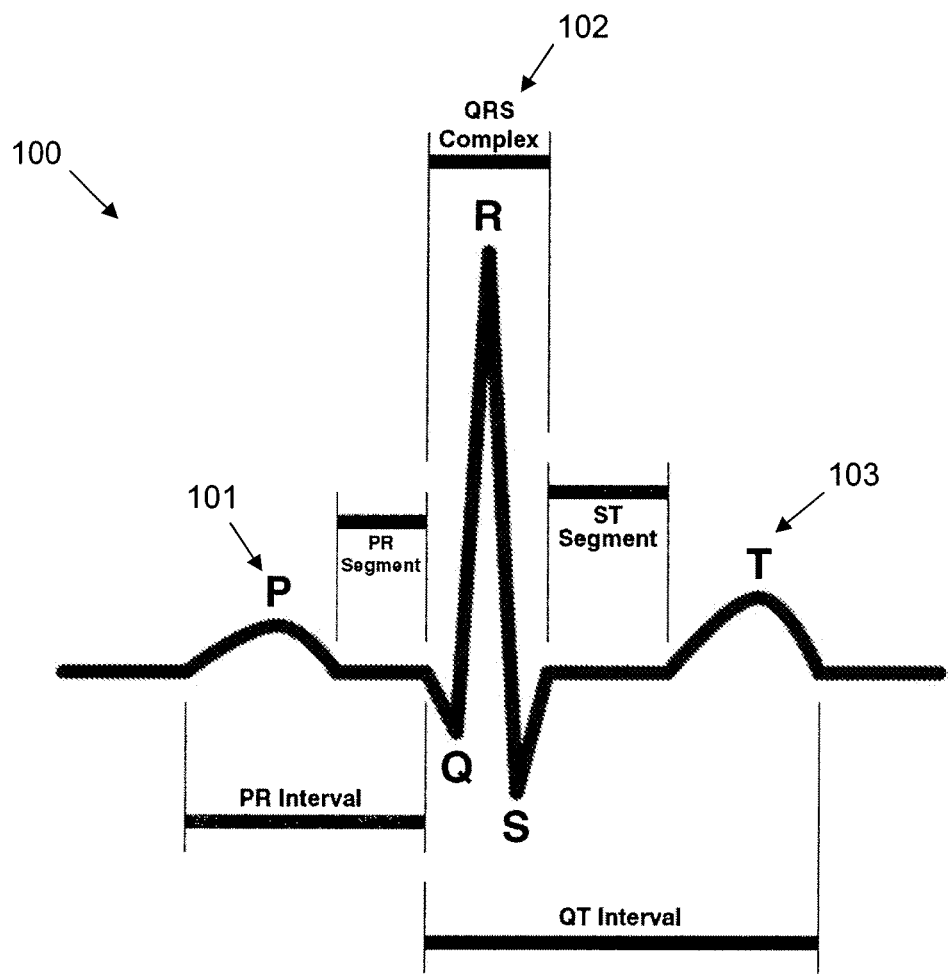
FIG. 1 depicts a typical electrocardiogram tracing of a normal heart beat known in the prior art.

Cardiac allograft rejection can be indicated by cardiac function. An electrocardiogram (ECG or EKG) is the primary tool to evaluate cardiac electrophysiology, and has a prime function in the screening and diagnosis of cardiovascular diseases. As shown in FIG. 1, a typical ECG tracing of a normal heartbeat 100 consists of a P wave 101, a QRS complex 102 and a T wave 103. The QRS complex 102 is a record of the measurement of the movement of electrical impulses through the lower heart chambers (ventricles), primarily in the Purkinje fibers. The depolarization phase (QRS) of the surface electrocardiogram is a sensitive indicator of myocardial damage, but traditionally has been disappointing in the diagnosis of cardiac allograft rejection.

Several systems, however, have attempted to use measurements of the electrical signals from a transplanted heart to predict cardiac rejection in transplant recipients. In these systems, either the rhythm of the transplanted heart, or the electrical signals from the cardiac allograft are closely monitored and analyzed to detect rejection of the cardiac allograft. In one study pacemaker leads were implanted into the cardiac allograft to measure and record the graft's electrical signals. For instance the pacemaker leads may measure the amplitude, width, time response, or interval of the T wave, which corresponds to repolarization of the graft's ventricles, or the QRS complex. In the study, the collected data was then transmitted to an implanted pacemaker or other device. The data may then be stored over time, such that the data can be analyzed over time and trends in the electrical characteristics of the cardiac allograft can be detected. These trends in the collected data can be compared with baseline data of the cardiac allograft, which is collected shortly after transplantation, to evaluate performance of the cardiac allograft and detect rejection of the graft.

The current invention provides advantages for detecting cardiac allograft rejection over prior art devices and methods. One advantage of the current inventive device is that the device does not require the implantation of pacemaker leads into the tissue of the cardiac allograft. As a result, the current inventive device has a reduced risk of infection after implantation, which risk is enhanced by immunosuppressive drugs given to transplant patients, making the device much less invasive. Moreover, the current inventive device correlates the electrical signal data from the cardiac allograft with other physiological data such as overall cardiac output, and core body temperature, to provide a more robust assessment of cardiac allograft rejection.

Figure 2:
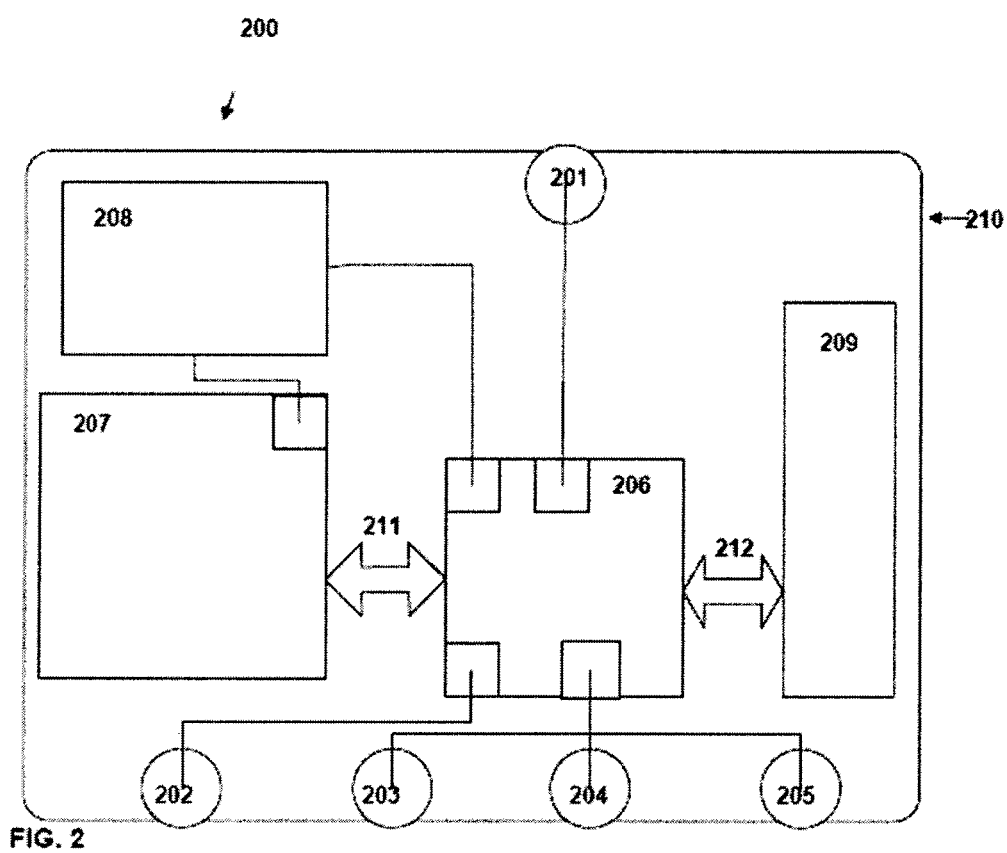
FIG. 2 depicts a device for detecting cardiac allograft rejection in accordance with an embodiment of the present invention.

In one embodiment, shown in FIG. 2, the inventive device 200 is composed of sensors 201-205, a processor 206, a local memory 207, a battery, or other power supplying components 208, and a transmitting component 209 contained within a water and air tight housing 210. The device is about 1.5 inches by 3 inches by 0.5 inches thick, although one of skill in the art will readily appreciate that larger sizes and smaller sizes are readily achievable. The device 200 can also have buses 211-212, or other connection components, between the processor 206 and local memory 207, and between the processor 206 and the transmitting device 209. In an alternate embodiment there may be a bus, or other connection components between the transmitting device 209 and the local memory 207. The device can be implanted under the skin of the thorax or abdomen. In one particular embodiment, the device is implanted in a patient's chest in a position similar to that of a common pacemaker. In this position, appropriate measurement of the cardiac allograft's electrical signals and other characteristics can be made. However, in alternate embodiments, the device may be implanted in locations throughout a patient's thorax or abdomen.

In one embodiment, the sensors 201-205 are incorporated on the surface of the air and water tight housing 210. In alternate embodiments, the sensors 201-205 may protrude slightly from the surface of the housing. The sensors can be a plurality of electrodes, which measure electrical activity (e.g., voltages) generated by the cardiac allograft, or the rate of change of these voltages such as the P wave 101, QRS complex 102 and T wave 103 of the ECG 100. One or more of these electrical sensors can also measure the overall impedance within the chest of the patient to determine the cardiac output of the allograft. As is known in the art, impedance changes in a patient's chest correspond to blood volume changes within the chest. Accordingly, measurement of split second impedance changes within the chest, as the heart beats, can be used to calculate both the cardiac output and lung water content. The sensors 201-205 can also include a sensor capable of measuring the core body temperature of the patient such as a thermocouple, thermistor, or resistance thermometer (all of which are well known in the art).

In a particular embodiment, the inventive device's combination of electrical sensors is used to collect baseline data from the transplanted allograft shortly after the transplant procedure. In one embodiment, the electrical sensors are used to measure the electrical activity of the cardiac allograft (e.g., voltages, QRS complex), cardiac output, core body temperature, or other physiological data ("Parameters"). The data should be collected under controlled conditions according to specified intervals and durations. For example, the data may be collected for thirty minutes a day over the period of one week, five days after the transplant procedure. The collected data are analyzed using statistical techniques known in the art to derive baseline average values ("Baseline Data") and standard deviations for the Parameters. The Baseline Data can then be stored in the local memory of the inventive device.

In one embodiment, the Baseline Data can be updated at regular intervals after the transplant procedure. For instance, every six months the updated data can be collected and analyzed according to the conditions and procedures used to initially collect the baseline data. After the updated data are collected, the average value and standard deviation data for the Parameters can be updated in the local memory of the inventive device. By updating the Baseline Data, the inventive device may better detect rejection of the cardiac allograft by adapting to the changing physiological conditions of the patient.

After Baseline Data are collected, the electrical sensors of the inventive device begin to measure the Parameters of the cardiac allograft at regular intervals. In one embodiment, measurement of the Parameters occurs daily. In alternate embodiments, the Parameters are measured more than once a day, or several times a week or month. The frequency of measurement can be tailored to fit the needs of the patient. During measurement, the electrical sensors of the inventive device measure the electrical activity of the cardiac allograft (e.g., voltages, QRS complex), the rate of change of the voltages, the impedance of the patient's chest, and the patient's core body temperature during a measurement interval; for example, over a set number of contraction cycles (e.g., 100 contraction cycle), or over a period of time. These measurements are processed by the processor of the inventive device using averaging techniques known in the art to determine the average electrical activity (e.g., average voltages, average QRS complex), cardiac output, and core body temperature during the Measurement Interval ("Average Parameter Values"). Averages can be the mean, median or mode. The processor may also use a filtration process to exclude variations in the QRS voltage due to cardiac arrhythmias and other outliers.

The Average Parameter Values can then be stored in the memory of the inventive device and compared with the Baseline Data. If a measured Average Parameter Value is different from the stored Baseline Data by a set amount, for example, more than two standard deviations, that particular Average Parameter Value may be annotated to warn that it is outside of the expected range. In one embodiment, the annotation can be an asterisk or other visual notation that will identify the Average Parameter Value upon review. In alternate embodiments, the annotation can be an auditory annotation, such as a beep or other audible clue.

Data stored in the device may be downloaded to an external system through transmission, such as radio frequency identification (RFID) system, Bluetooth, WiFi or other transmitting methods known in the art. In one embodiment, shown in FIG. 3, an RFID system is used to transmit the Average Parameter Values from the inventive device 200 to an external device 301. In this embodiment, the transmitting component includes an RFID transponder 209 coupled to the processor of the inventive device. In an alternate embodiment (not shown), the RFID unit 209 of the inventive device is active and is directly coupled to both the inventive device's power supply component 208 and memory component 207. In response to a signal 303a emitted by an external interrogator 302, data stored on the local memory of the inventive device is downloaded 303b to the external device 301.

These downloads may occur at regular, pre-determined intervals after the transplant procedure, or as needed if symptoms indicating rejection arise. For example, Average Parameter Values can be downloaded from the inventive device every two weeks after the transplant for the first two months, extending to every month for the first six months, and every six months thereafter. Moreover, the frequency of downloads can be tailored to the individual needs of the patient. The data can be transmitted to a receiver worn by the patient. Such a receiver can contain retransmission capabilities (such as a cell phone) to report the data to a remote health care provider. Alternately, the receiver can be connectable to the Internet to make a remote report. Although the data can also be downloaded in a physician's office, remote data collectors allow data to be automatically sent to the health care provider without a need for an office visit. Remote transmission could be triggered by any measurements that exceeded the baseline data, particularly measurements that are more than two standard deviations from the baseline data, so that the health care provider would be immediately informed of any change in the patient's condition.

After the information is downloaded, the data may be analyzed according to known statistical techniques to determine whether the measured Average Parameter Values indicate that an acute or chronic rejection processes are under way. For instance, if there are a statistically significant number of Average Parameter Values that lie outside two standard deviations from the Baseline Data, this may indicate an acute or chronic rejection episode. In response, the dosage of the patient's immunosuppressant therapy can be increased to effectively treat the rejection episode. Moreover, the download frequency from the inventive device can be increased to monitor the efficacy of immunosuppressant therapy and to guide the dosage of immunosuppressant drugs after the rejection episode is effectively treated.

One exemplary method for detecting cardiac allograft rejection in a subject is shown in FIG. 4. After the subject receives the cardiac allograft, Baseline Data regarding the subject and the cardiac allograft are collected 401. Physiological parameters (e.g., electrical activity generated by the cardiac allograft, voltages generated by the cardiac allograft, rate of changes of the voltages generated by the cardiac allograft, impedance within the chest of the recipient to determine cardiac output and/or lung water content, and the recipient's core body temperature) are measured during a measurement interval 402. The physiological parameters are processed to determine the average parameter values 403. The average parameter values are compared with the baseline data 404. Optionally, if an average parameter value differs by more than one standard deviation, the value is annotated 405. The average parameter values are analyzed to determine if there is a statistically significant deviation from the Baseline Data 406. If a statistically significant deviation from the Baseline Data is present, there is an indication of an acute or a chronic rejection of the cardiac allograft 407. If no statistically significant deviations are present, no action is necessary 408.

EXAMPLE

The following example is provided to better illustrate the claimed invention and is not to be interpreted as limiting the scope of the invention. To the extent that specific materials are mentioned, it is merely for purposes of illustration and is not intended to limit the invention. One skilled in the art may develop equivalent means or materials without the exercise of inventive capacity and without departing from the scope of the invention.

The device as described herein is provided and implanted within a cardiac transplant recipient. Five days after the cardiac transplant, data regarding the electrical activity generated by the cardiac allograft, voltages generated by the cardiac allograft, rate of changes of the voltages generated by the cardiac allograft, impedance within the chest of the recipient (to determine cardiac output and/or lung water content), and the recipient's core body temperature (physiological parameters) are collected. The data are collected thirty minutes a day for one week. The average values for the data is calculated to establish the Baseline Data. The standard deviations for each parameter are also calculated. The device measures the physiological parameters for an interval of 100 cardiac contractions and calculates the average value of each parameter. Thereafter, it is determined that the impedance within the chest differs by two standard deviations from the Baseline Data. Accordingly, the device sends a signal indicating the irregular value to an external device. The external device notifies a medical practitioner that an irregular value is detected. Alternatively, the medical practitioner checks the external device once a month to monitor the number of times and extent the parameters deviate from the Baseline Data. The transplant recipient's immunosuppressant therapy is adjusted based on the information collected by the device.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method for detecting cardiac allograft rejection in a subject that has received a cardiac allograft, comprising:
    determining baseline data regarding the subject and the cardiac allograft;
    measuring parameters of the cardiac allograft during a measurement interval;
    determining average parameter values for the parameters during the measurement interval; and
    comparing the average parameter values with the baseline data to detect the presence of a cardiac allograft rejection;
    wherein the parameters comprise: impedance within the chest measured without implanting leads into the tissue of the cardiac allograft, electrical activity generated by the cardiac allograft, at least one voltage generated by the cardiac allograft, rate of change of the at least one voltage generated by the cardiac allograft, and body temperature.

2. The method of claim 1, further comprising providing an implantable device for detecting rejection of the cardiac allograft in the subject, comprising:
    a plurality of sensors to measure the at least one parameter;
    a processor in electronic communication with the plurality of sensors, the processor configured to receive at least one measured parameter;
    a memory component to store the baseline data, data corresponding to the at least one measured parameter and/or data corresponding to the at least one average parameter value; and
    a power supply component to provide electricity to components of the implantable device.

3. The method of claim 1, further comprising determining a presence of a statistically significant deviation from the baseline data, whereby the presence of the statistically significant deviation is indicative of an acute or a chronic rejection episode.

4. The method of claim 1, further comprising annotating the at least one average parameter value if the at least one parameter value differs by more than one standard deviation from the baseline data.

5. The method of claim 1, further comprising annotating the at least one average parameter value if the at least one parameter value differs by more than two standard deviations from the baseline data.

6. The method of claim 1, wherein collecting the data used to determine the baseline data begins about five days after a cardiac allograft transplant procedure.

7. The method of claim 1, wherein determining the baseline data comprises collecting data for about thirty minutes a day for a period of about one week and determining the average values of the data.

8. The method of claim 1, wherein the measurement interval is selected from the group consisting of about 50, 100, 200, 300, 400, 500, and 1000 contraction cycles of the cardiac allograft.

9. The method of claim 8, wherein the measurement interval is about one hundred contraction cycles of the cardiac allograft.

10. The method of claim 1, wherein the measurement interval is selected from the group consisting of about 0.5, 1, 2, 3, 4, 5, 10, 15, 20, 30, 45, and 60 minutes.

11. The method of claim 1, wherein the impedance within the chest is used to calculate cardiac output, lung water content or both.

12. An implantable device for detecting cardiac allograft rejection in a subject that has received a cardiac allograft, comprising:
a plurality of sensors to measure parameters;
a processor in electronic communication with the plurality of sensors, the processor configured to receive the measured parameters;
a memory component to store baseline data, data corresponding the measured parameters and/or data corresponding average parameter values;
a power supply component to provide electricity to components of the implantable device; and
a housing to encapsulate components of the implantable device,
wherein the parameters comprise: impedance within the chest measured without implanting leads into the tissue of the cardiac allograft, electrical activity generated by the cardiac allograft, at least one voltage generated by the cardiac allograft, rate of change of the at least one voltage generated by the cardiac allograft, and body temperature.

13. The implantable device of claim 12, further comprising a transmitting component to transmit the data corresponding to the at least one measured parameter to an external device.

14. The implantable device of claim 12, wherein at least one sensor measures the body temperature and is selected from the group consisting of a thermocouple, a thermistor, a resistance thermometer and combinations thereof.

15. The implantable device of claim 12, wherein the processor is further configured to determine the at least one average parameter value for the at least one parameter during a measurement interval.

16. The implantable device of claim 15, wherein the measurement interval is selected from the group consisting of about 50, 100, 200, 300, 400, 500, and 1000 contraction cycles of the cardiac allograft.

17. The implantable device of claim 16, wherein the measurement interval is about one hundred contraction cycles of the cardiac allograft.

18. The implantable device of claim 15, wherein the measurement interval is selected from the group consisting of about 0.5, 1, 2, 3, 4, 5, 10, 15, 20, 30, 45, and 60 minutes.

19. An external device adapted to communicate with an implantable device for detecting cardiac allograft rejection, the implantable device comprising:
a plurality of sensors to measure parameters;
a processor in electronic communication with the sensors, the processor configured to receive the measured parameters; and
a memory component to store baseline data, data corresponding measured parameters and/or data corresponding to average parameter value,
wherein the parameters comprise: impedance within the chest measured without implanting leads into the tissue of the cardiac allograft, electrical activity generated by the cardiac allograft, at least one voltage generated by the cardiac allograft, rate of change of the at least one voltage generated by the cardiac allograft, and body temperature.

20. The external device of claim 19, further adapted to receive and analyze the at least one average parameter value to determine a presence of a statistically significant deviation from baseline data, whereby the presence of the statistically significant deviation is indicative of an acute or chronic rejection episode.

21. The external device of claim 19, further adapted to receive information regarding the presence of a statistically significant deviation from the baseline data that is indicative of an acute or chronic rejection episode.

22. The external device of claim 19, further adapted to provide an alert regarding the rejection of the cardiac allograft.

23. A system for detecting cardiac allograft rejection in a subject that received a cardiac allograft, comprising:
an implantable device for detecting cardiac allograft rejection, comprising:
a plurality of sensors to measure parameters,
a processor in electronic communication with the plurality of sensors, the processor configured to receive the measured parameters,
a memory component to store baseline data, data corresponding the measured parameters and/or data corresponding to average parameter values,
a power supply component to provide electricity to components of the implantable device, and
a housing to encapsulate components of the implantable device,
wherein parameters comprise; impedance within the chest measured without implanting leads into the tissue of the cardiac allograft, electrical activity generated by the cardiac allograft, at least one voltage generated by the cardiac allograft, rate of change of the at least one voltage generated by the cardiac allograft, and body temperature; and
an external device adapted to communicate with the implantable device.

24. The system of claim 23, wherein at least one sensor measures the body temperature and is selected from the group consisting of a thermocouple, a thermistor, a resistance thermometer and combinations thereof.

25. The system of claim 23, wherein the processor is further configured to determine at least one average parameter value for the at least one parameter during a measurement interval.

26. The system of claim 25, wherein the measurement interval is selected from the group consisting of about 50, 100, 200, 300, 400, 500, and 1000 contraction cycles of the cardiac allograft.

27. The system of claim 26, wherein the measurement interval is about one hundred contraction cycles of the cardiac allograft.

28. The system of claim 25, wherein the measurement interval is selected from the group consisting of about 0.5, 1, 2, 3, 4, 5, 10, 15, 20, 30, 45, and 60 minutes.

29. The system of claim 23, wherein the external device is further adapted to receive and analyze the at least one average parameter value to determine a presence of a statistically significant deviation from baseline data, whereby the presence of the statistically significant deviation is indicative of an acute or chronic rejection episode.

30. The system of claim 23, wherein the external device is further adapted to receive information regarding the presence of a statistically significant deviation from the baseline data that is indicative of an acute or chronic rejection episode.

31. The system of claim 23, wherein the external device is further adapted to provide an alert regarding the rejection of the cardiac allograft.

32. A non-transitory computer readable medium to detect cardiac allograft rejection in a subject that has received a cardiac allograft, comprising computer executable components for:
   determining baseline data regarding the subject and the cardiac allograft;
   measuring parameters of the cardiac allograft during a measurement interval;
   determining average parameter values for the parameters during the measurement interval; and
   comparing the average parameter values with the baseline data to detect the presence of a cardiac allograft rejection,
   wherein the parameters comprise: impedance within the chest measured without implanting leads into the tissue of the cardiac allograft, electrical activity generated by the cardiac allograft, at least one voltage generated by the cardiac allograft, rate of change of the at least one voltage generated by the cardiac allograft, and body temperature.

33. The non-transitory computer readable medium of claim 32, further comprising a computer executable component for determining a presence of a statistically significant deviation from the baseline data, whereby the presence of the statistically significant deviation is indicative of an acute or a chronic rejection episode.

34. The non-transitory computer readable medium of claim 32, further comprising a computer executable component for annotating the at least one average parameter value if the at least one parameter value differs by more than one standard deviation from the baseline data.

35. The non-transitory computer readable medium of claim 32, further comprising a computer executable component for annotating the at least one average parameter value if the at least one parameter value differs by more than two standard deviations from the baseline data.

36. The non-transitory computer readable medium of claim 32, wherein the measurement interval is selected from the group consisting of about 50, 100, 200, 300, 400, 500, and 1000 contraction cycles of the cardiac allograft.

37. The non-transitory computer readable medium of claim 36, wherein the measurement interval is about one hundred contraction cycles of the cardiac allograft.

38. The non-transitory computer readable medium of claim 32, wherein the measurement interval is selected from the group consisting of about 0.5, 1, 2, 3, 4, 5, 10, 15, 20, 30, 45, and 60 minutes.

39. The non-transitory computer readable medium of claim 32, further comprising a computer executable component for calculating cardiac output, lung water content or both.

* * * * *